(12) United States Patent
Ricci et al.

(10) Patent No.: US 7,200,435 B2
(45) Date of Patent: Apr. 3, 2007

(54) NEURAL NETWORK BASED LEARNING ENGINE TO ADAPT THERAPIES

(75) Inventors: Carlos Ricci, Apple Valley, MN (US); Surekha Palreddy, Mission Viejo, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 576 days.

(21) Appl. No.: 10/668,428

(22) Filed: Sep. 23, 2003

(65) Prior Publication Data

US 2005/0065569 A1     Mar. 24, 2005

(51) Int. Cl.
*A61N 1/362* (2006.01)

(52) U.S. Cl. .......................................................... 607/9

(58) Field of Classification Search .............. 607/4–26, 607/30–32, 60, 59
See application file for complete search history.

(56) References Cited

U.S. PATENT DOCUMENTS

| | | | |
|---|---|---|---|
| 5,251,626 A | 10/1993 | Nickolls et al. | |
| 6,263,238 B1 | 7/2001 | Brewer et al. | |
| 6,443,889 B1* | 9/2002 | Groth et al. | 600/300 |
| 6,839,581 B1* | 1/2005 | El-Solh et al. | 600/324 |
| 2002/0083025 A1* | 6/2002 | Robarts et al. | 706/12 |

OTHER PUBLICATIONS

Javed Khan et al. "Classification and diagnostic prediction of cancers using gene expression profiling and artificial neural networks,", Nature Medicine Jun. 2001, vol. 7, No. 6.

Bernd Fritzke, "Some Competitive Learning Methods", Draft from Apr. 5, 1997.

Yudong D. He & Stephen H. Friend, Microarrays—the 21st Century Diving Rod?, Nature Medicine, Jun. 2001, vol. 7 No. 6.

* cited by examiner

*Primary Examiner*—George R. Evanisko
(74) *Attorney, Agent, or Firm*—Schwegman, Lundberg, Woessner, & Kluth, P.A.

(57) ABSTRACT

A cardiac device system for implementing a cardiac device having adaptive treatment therapies utilizing a neural network based learning engine includes an implantable cardiac device module and an external data processing system for specifying the operating characteristics of the cardiac device module. Both the cardiac device module and the external processing system possess an artificial neural network to specify the operation of the cardiac device module as it provides adaptive treatment therapies. The external data processing system includes a complete neural network module that trains and validates the operation of the neural network to match the optimal treatment options with a received set of collected patient data. In contrast, a runtime neural network module that only provides real time operation of the neural network using collected patient data is located within the cardiac device module. The cardiac device module and the external processing module communicate with each other to pass collected patient data from the cardiac device module to the external processing system when the operation of the neural network is to be updated. The cardiac device module and the external processing module also communicate with each other to pass operating coefficients for the neural network back from the external processing system to the cardiac device module once these coefficients are updated.

14 Claims, 7 Drawing Sheets

Fig. 1

ANN Computer

NEURAL NETWORK BASED LEARNING ENGINE TO ADAPT THERAPIES

TECHNICAL FIELD

This application relates in general to a method, apparatus, and article of manufacture for providing adaptive medical therapies utilizing a neural network based learning engine, and more particularly to a method, apparatus, and article of manufacture for implementing an implantable cardiac device having adaptive treatment therapies utilizing a neural network based learning engine.

BACKGROUND

Implantable cardiac device have recently become increasingly commonplace in providing cardiac therapies to patients in need of constant monitoring of heart conditions that require immediate treatment. These cardiac devices typically provide a single therapy, or at most a few different therapies, to a patient depending upon a small set of observable parameters regarding the condition of a patient's heart. As a result of the more widespread use of such devices, it is becoming more evident that the operation of these devices need to be customized to provide a more optimal set of therapies to any given patient.

The computational capabilities inherent within implantable devices has increased along with the general increase in computational technology during this same time period. However, performing more complex computations also results in increased power consumption on any given computational platform, including the devices within implantable systems. As a result, many data processing strategies have not been readily utilized in these devices as the computational requirements of such systems has typically been too complex to be realistically utilized.

SUMMARY

This application relates in general to a method, apparatus, and article of manufacture for providing adaptive medical therapies utilizing a neural network based learning engine. One possible embodiment of the present invention is a system providing adaptive medical therapies utilizing a neural network based learning engine to a cardiac patient. The system includes a cardiac devices module for providing adaptive medical therapies to the patient, an artificial neural network processing module for training and validating the operation of a neural network, and a communications link between the cardiac device module and the artificial neural network processing module. The cardiac device module includes a cardiac devices data collection module for collecting patient data associated with the cardiac health state of the patient's heart, a cardiac therapy module for applying corrective medical therapies to the patient's heart upon detection of undesired health conditions, and a runtime neural network module for processing collected patient data to determine the corrective medical therapies to be applied using the cardiac therapy module. The artificial neural network processing module includes a cardiac neural network training module for processing collected patient data to determine a set of operating coefficients used by the artificial neural network when determining optimal treatment therapies, a cardiac device interface module for receiving collected patient data from the cardiac device module and for transmitting the set of operating coefficients associated used by the artificial neural network when determining optimal treatment therapies and a collected patient data history data store for maintaining all of the patient collected data history and treatment therapies. The cardiac device runtime neural network module and the neural network training module implement identical networks of nodes.

DETAILED DESCRIPTION

This application relates in general to a method, apparatus, and article of manufacture for providing adaptive medical therapies utilizing a neural network based learning engine. In the following detailed description of exemplary embodiments of the invention, reference is made to the accompanied drawings, which form a part hereof, and which is shown by way of illustration, specific exemplary embodiments of which the invention may be practiced. These embodiments are described in sufficient detail to enable those skilled in the art to practice the invention, and it is to be understood that other embodiments may be utilized, and other changes may be made, without departing from the spirit or scope of the present invention. The following detailed description is, therefore, not to be taken in a limiting sense, and the scope of the present invention is defined only by the appended claims.

Throughout the specification and claims, the following terms take the meanings explicitly associated herein, unless the context clearly dictates otherwise. The term "connected" means a direct connection between the items connected, without any intermediate devices. The term "coupled" means either a direct connection between the items connected, or an indirect connection through one or more passive or active intermediary devices. The term "circuit" means either a single component or a multiplicity of components, either active and/or passive, that are coupled together to provide a desired function. The term "signal" means at least one current, voltage, or data signal. Referring to the drawings, like numbers indicate like parts throughout the views.

Figure 1:
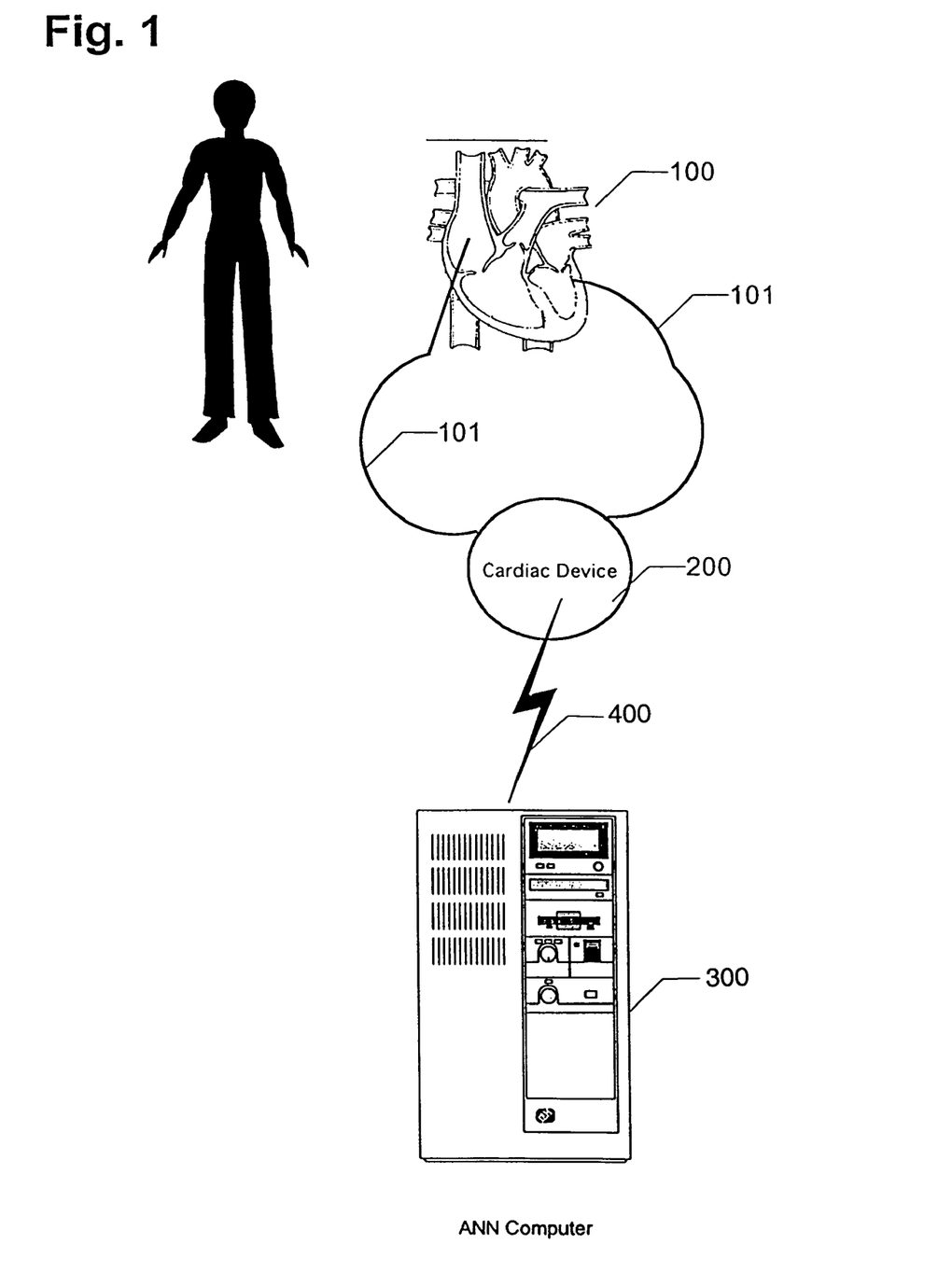
FIG. 1 illustrates an example embodiment of a cardiac device system having adaptive treatment therapies utilizing a neural network based learning engine according to one possible embodiment of the present invention.

FIG. 1 illustrates an example embodiment of a cardiac device system having adaptive treatment therapies utilizing a neural network based learning engine according to one possible embodiment of the present invention. The cardiac device system includes a cardiac device 200 electronically connected to a patient's heart 100 using electrical connections 101 to obtain data associated with a collection of observable parameters related to the health of the heart 100 as well as provide a collection of medical therapies as needed to maintain a healthy operation for the heart. The cardiac device 200 contains a set of data operating parameters associated with providing these collection of medical therapies that are used to control the operation of the cardiac device when it provides these collection of medical therapies to the heart 100 based upon the collection of observable parameters measured by the cardiac device 200.

The data operating parameters associated with providing the collection of medical therapies may be adjusted periodically to provide a patient with a more optimal set of therapies for a given set of observed parameters for the operation of the patient's heart 100. Types of therapies may include, but is not limited to: pacing at physiological rates to correct a heartbeat that is too slow (pacemaker therapy: PM), pacing at physiological rates to correct for dissynchrony between the contractions of the left and right ventricles (heart failure therapy or cardiac resynchronization therapy: HF/CRT), pacing at high rates to break cycles of tachycardia (anti-tachycardia pacing: ATP), and shock therapy to break tachycardia, particular fibrillation (defibrillation shock or shock). For PM and HF/CRT, the cardiac device typically provides a continuous series of pulses, low voltage and narrow in time, just strong enough to stimulate the heart into contraction at controlled times or intervals. For ATP, the cardiac device typically provides a burst or set of bursts of narrow pulses at higher voltages. For shock, the cardiac device typically provides a high-voltage pulse of characteristic width and shape. In the case of cardiac devices having ATP and/or shock therapy available, the devices are typically designed to respond with appropriate therapy when tachycardia or fibrillation is detected. The therapies may be applied to the atria or the ventricles of the heart, or both, as indicated by the underlying condition of the heart.

One skilled in the art will recognize that many therapy parameters are typically provided for adjusting corrective therapies to best treat the condition of individual patients. Examples may include but not be limited to, the lower rate limit (LRL), atrio-ventricular (AV) delay, maximum tracking rate (MTR), pulse width, and pulse voltage for PM and HF/CRT; the burst cycle length (BCL), number of pulses per burst, number of burst per attempt, change in BCL per burst, and pulse width and voltage for ATP; and energy, polarity, waveform (monophasic or biphasic), and duty cycle (percentage of discharge time spent in one polarity of a biphasic waveform) for shock. The values of the applicable therapy parameters, in conjunction with the patient's observed parameters, are provided to an ANN processing system. Values stored in cardiac device 200 are provided to the ANN processing system 300 over communications link 400. Observed parameters for the patient may be associated with past therapy attempts, both those existing before the therapy and those existing in response to this therapy, or may include general trending information in the patient's history, not directly associated with a particular therapy attempt. The ANN processing system 300 then determines an optimized set of applicable therapy parameters and communicates them to the cardiac device 200 over communications link 400.

The communications link 400 may consist of any electrical communications link between the processing devices within the cardiac device 200 and the ANN processing system 300. One skilled in the art will recognize that such a link may be constructed using an RF communications link, an IR communications link, an electrical communications link, an audio based communications link, or any other communications link that provides digital communications between these devices without deviating from the spirit and scope of the present invention as recited within the attached claims.

Figure 2:
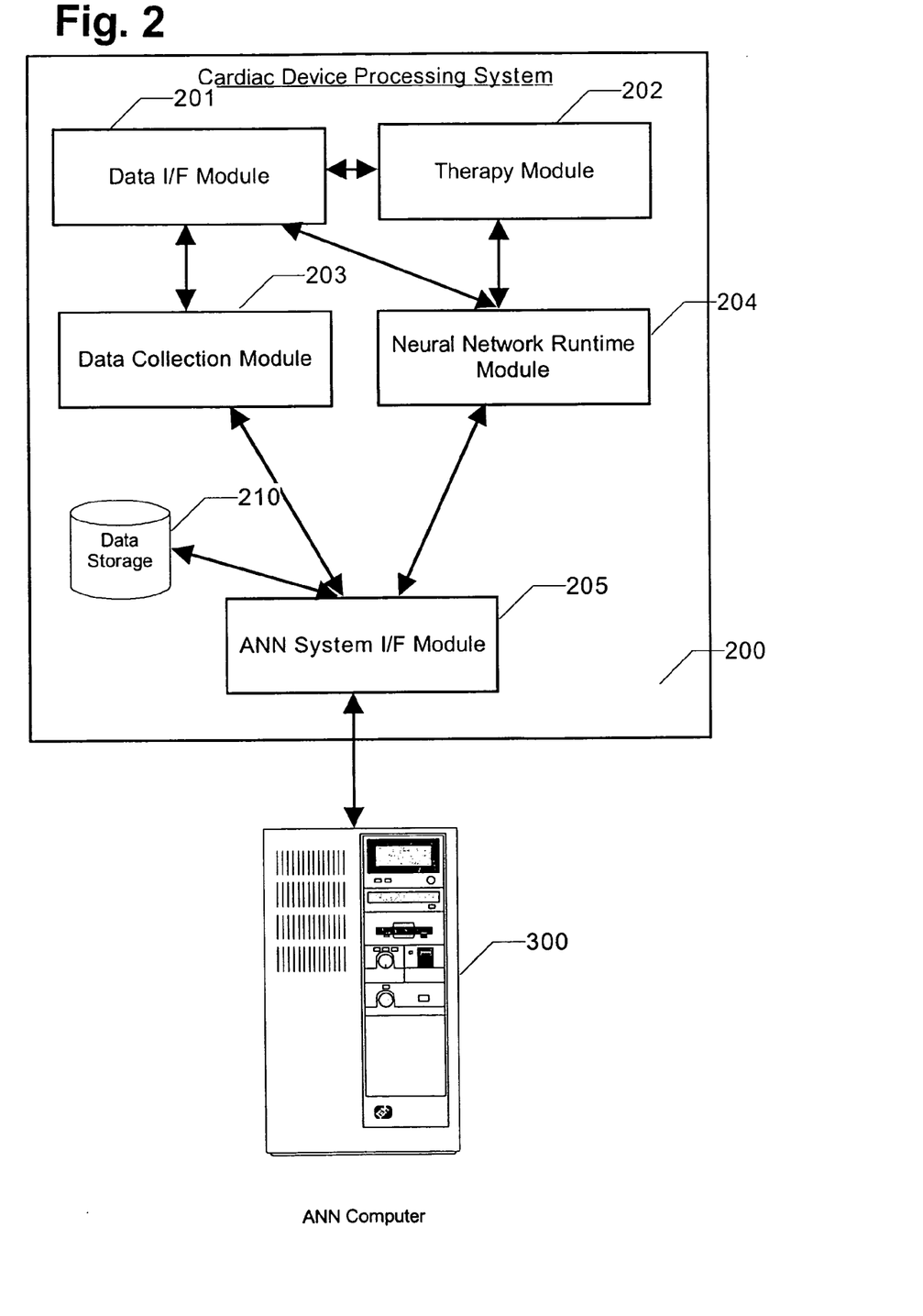
FIG. 2 illustrates an example embodiment of a cardiac device module that is part of an overall system for providing adaptive treatment therapies utilizing a neural network based learning engine according to one possible embodiment of the present invention.

FIG. 2 illustrates an example embodiment of a cardiac device module that is part of an overall system for providing adaptive treatment therapies utilizing a neural network based learning engine according to one possible embodiment of the present invention. The cardiac device module 200 includes a set of processing modules to perform the operations associated with collecting data, providing therapies and communicating with the ANN processing system 300. These processing modules include a cardiac data interface module 201, a cardiac therapy module 202, a cardiac device data collection module 203, a cardiac neural network runtime module 204, an ANN processing system interface module 205 and a local data storage module 210.

The cardiac data interface module 201 interfaces the cardiac device module 200 to the patient's heart 100 to collect data regarding the current health of the heart. This data may include but is not limited to a collection of observable parameters such as values for an A Rate, a V Rate, an A Rate dispersion, a V Stability, an AV pattern, an NSR template, an arrhythmia template, a detected or classified depolarization morphology, a measure of patient activity such as derived from a Minute Ventilation (MV) sensor and/or an accelerometer, a measure of hemodynamic function such as derived from a hemodynamic sensor, a number of past attempts required to treat a given observed condition, an identification of a particular therapy that provided an effective treatment of an observed condition, an identification of a particular therapy that provided an ineffective treatment of an observed condition, an age of a patient, an identification of medications known to be taken by the patient, etc and other environmental factors, including patient's age, gender, and vital statistics at last observed exertion.

The cardiac therapy module 202 provides the medical therapies by cardioverting/defibrillating a heart. This module obtains its operating instructions from the cardiac neural network runtime module 204 to provide either no therapy when no therapy is warranted or when noise is observed, to provide one or more therapies from the collection of medical therapies as defined previously in an optimal or most efficient manner depending upon the collection of observable parameters.

The cardiac device data collection module 203 collects values observed by the cardiac data interface module 201 immediately preceding and during an event that gives rise to the cardiac therapy module 202 providing therapies to a patent. These collected values are stored within the local data storage module 210 for later use. These values are typically transmitted to the ANN processing system to update the operating parameters associated with the therapies; however, such collected values may also be used by various cardiac device modules during the operation of the cardiac device 200. For example, the collected values may include an indication of the last successful therapy to correct a particular observed condition. This last successful therapy may be utilized as a first attempted therapy if the particular observed condition recurs at a later date and time.

The cardiac neural network runtime module 204 and ANN processing system interface module 205 provide a mechanism for determining a course of treatment to deliver an optimal therapy to a patient for a given set of observed conditions. In the system according the present invention, a run-time only version of an artificial neural network is included within the cardiac device 200. The runtime version of the neural network accepts input data associated with observed conditions of a patient's heart and generates a particular therapy or sequence of therapies to be utilized to correct the observed condition. The runtime module is contrasted with the neural network training module found within the ANN processing system 300 that analyzes the data collected in the cardiac device data collection module 203 to determine a particular therapy or sequence of therapies to be utilized.

The artificial neural network disclosed herein corresponds to a generic neural network of no particular topology for the network of nodes contained therein. The neural network typically utilizes a form of competitive learning for the operation of the nodes within the network. Within these learning networks, a large number of data vectors are distributed in a high-dimensional space. These data vectors represent known values for experimental data that typically reflect a probability distribution of the input observed data. From this probability distribution representation, predictions for unknown values for similar input data may be determined.

In all of these learning networks, the networks are typically presented a set of input data that possesses a corresponding set of results data. From these data values, the network of nodes "learns" a relationship between the input data and its corresponding results data. In this process, the probability distribution relationship is estimated using the multi-dimensional network of nodes. This relationship is represented within a set of artificial neural network coefficients for a particular topology of nodes.

One skilled in the art will recognize that competitive learning networks include a nearly infinite number of network topologies that may be used to represent a particular probability distribution relationship without deviating from the spirit and scope of the present invention as recited within the attached claims. In addition, artificial neural networks may utilize various well-known algorithm architectures, including hard-competitive learning (i.e. "winner-take-all" learning), soft competitive learning without a fixed network dimensionality, and soft competitive learning with a fixed network dimensionality, to specify an artificial neural network according to the present invention as recited within the attached claims. Each of these algorithm architectures represents the same probability distribution relationship; however each of the various algorithm architectures better optimize corresponding processing parameters which are often mutually exclusive with each other. These parameters include error minimization or the minimization of an expected quantization error, entropy maximization for the reference vectors used within a network, and topology-preserving or feature mapping architectures that attempt to map high-dimensional inputs signals onto lower-dimensional structures in a manner that attempts to preserve similar relationships found within the original data within the post-mapping data. As such, any of these types of algorithm architectures may be used to construct an artificial neural network without deviating from the spirit and scope of the present invention as recited within the attached claims.

The ANN processing system interface module 205 provides the data communications functions between the cardiac device 200 and the ANN processing system 300 over the communications link 400. This module transfers the collected data from the data storage module 210 to the ANN processing system 300. This module 205 also accepts parameters used by the cardiac neural network runtime module 204 from the ANN processing system 300 after updated parameters are generated.

Figure 3A:
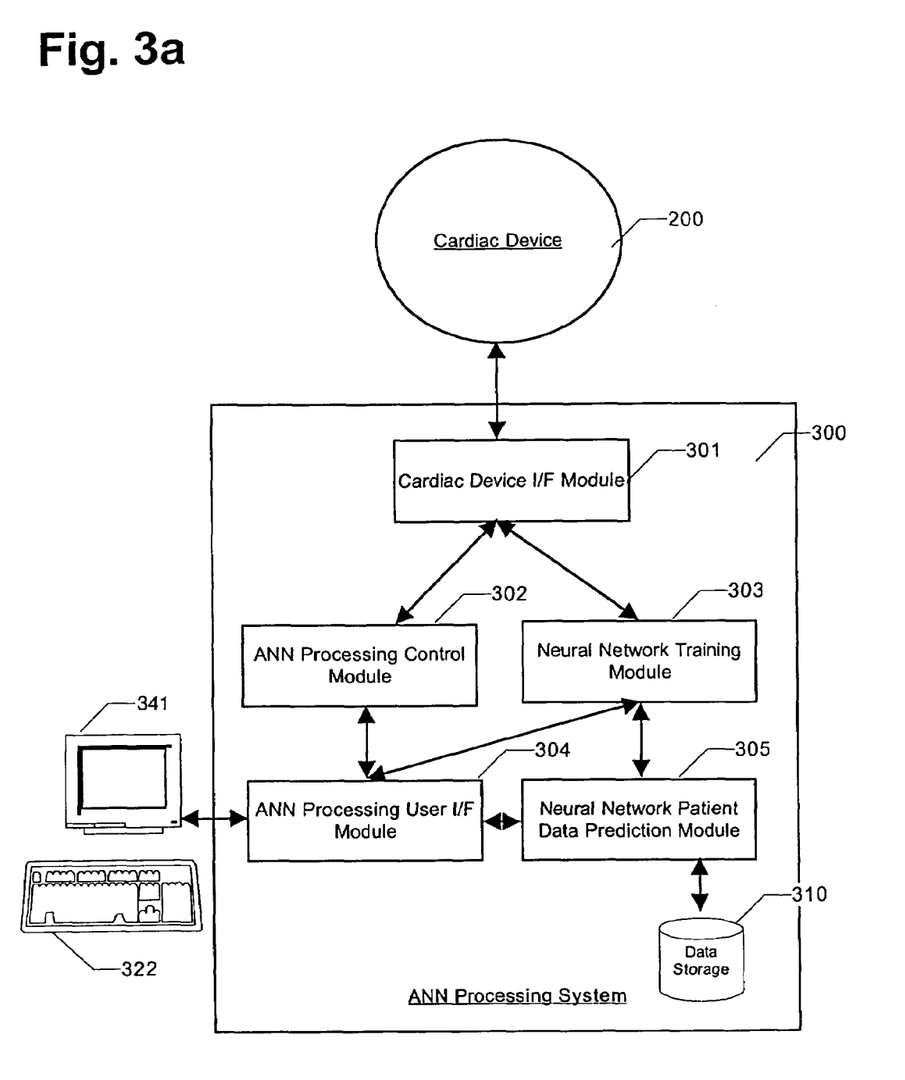
FIG. 3a illustrates an example embodiment of an artificial neural network server module for use with a cardiac device module that is part of an overall system for providing adaptive treatment therapies utilizing a neural network based learning engine according to one possible embodiment of the present invention.

FIG. 3a illustrates an example embodiment of an artificial neural network server module for use with a cardiac device module that is part of an overall system for providing adaptive treatment therapies utilizing a neural network based learning engine according to one possible embodiment of the present invention. The artificial neural network processing system 300 comprises a training module 303, a prediction module 305, and a database of network node coefficients 310. The training module 303 is used with a set of collected data that possesses a corresponding set of observed parameter values obtained by the cardiac device module 200 to generate a set of network node coefficients that represent a probability distribution relationship for an observed parameter data—observed results data set for a particular neural network topology and algorithm architecture. The training module 303 includes a data learning input module that receives the observed parameter data—observed results data set generated using the learning process described above. The training module 303 also includes an ANN node training module that processes the observed parameter data—observed results data set to generate the coefficients used to specify the probability distribution relationship and an ANN coefficient storage module 310 for storing the coefficients that have been previously generated for later use.

Figure 3B:
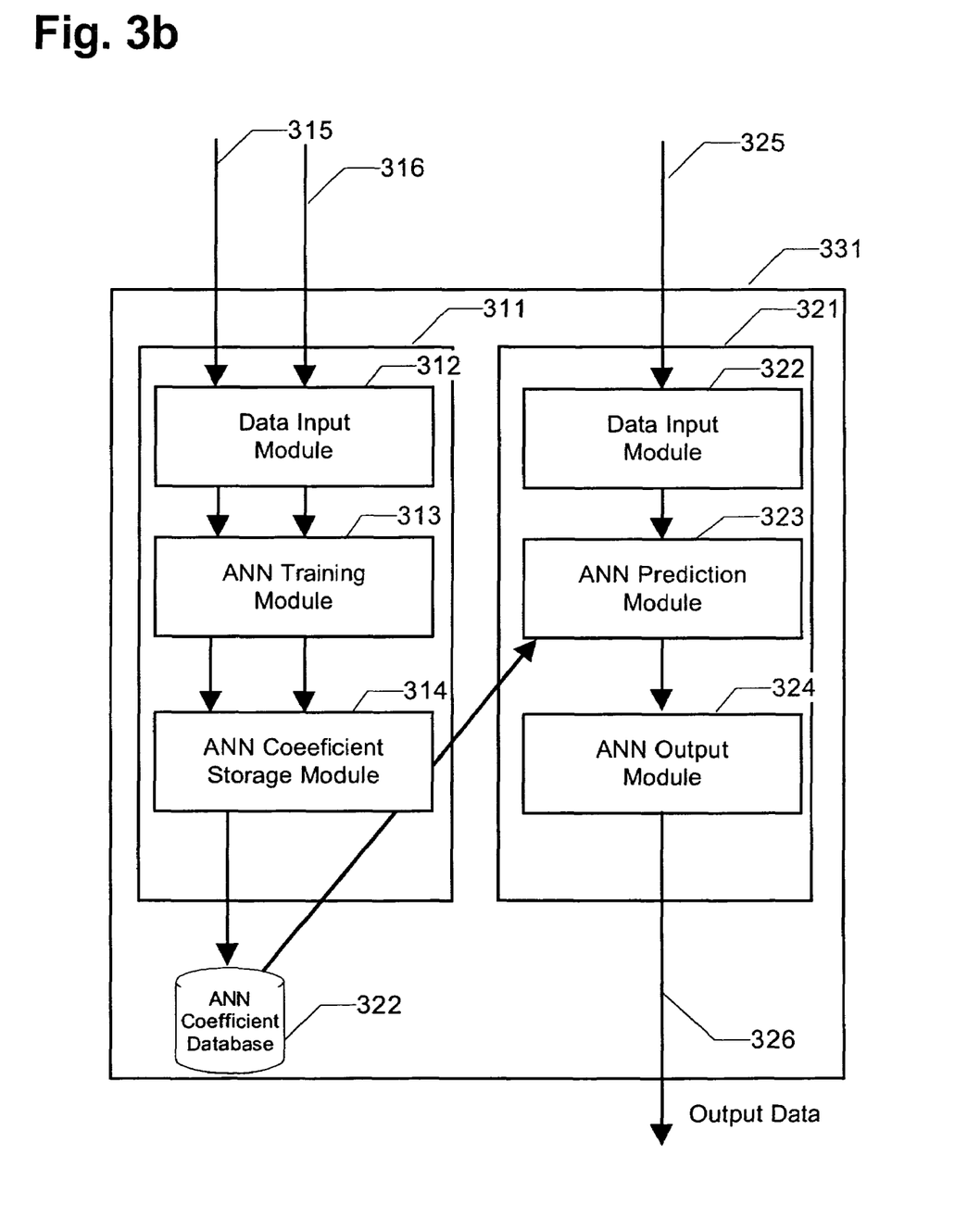
FIG. 3b illustrates a cardiac device processing system according to an example embodiment of the present invention.

The data processing within the training module 303 may proceed in a batch processing fashion in which all of the vectors within the observed parameter data—observed therapy data set are processed at a single time. In such a process, the observed parameter data—observed therapy data set is received by the interface module 301 from the cardiac device 200, processed by the training module 303, and the generated coefficients are placed within the database 310 by the prediction module 305. Alternatively, the observed parameter data—observed therapy data set may be processed as a sequence of smaller data sets in which the observed parameter data 315-observed therapy parameter 316 data set data values are generated at different times. In such a process, the training module 303 uses the previously stored coefficients retrieved by the storage module along with a new small data set provided by the input module 312 to generate an updated set of coefficients as shown in FIG. 3b. These updated coefficients may be once again stored within the database 310 for use at a later time.

FIG. 3b illustrates an artificial neural network 331 implemented as a set of processing modules according to the present invention. Once an artificial neural network 331 has been trained as discussed above, a prediction module 321 may be used to predict, or classify, a particular test data value 325. The prediction module 321 includes a data prediction input module 322, an ANN prediction module 323, and an ANN output module 324. The data prediction input module 322 receives the input test data generated as described above for use in the prediction module. The ANN prediction module 323 receives and utilizes the network coefficient values for the neural network from the ANN coefficient database 332 to predict the possible result for the probability distribution relationship specified within the neural network. This output value 326 is used by the ANN prediction module 305 to determine all possible values for a given observed therapy parameter, to determine an output set of therapy parameter value. This slope value is then output for later use in ranking and classifying the individual therapies used to determine preferred course of therapy for any given observed condition.

The operation of the ANN processing system 300 typically involves an operator connecting the ANN processing system 300 to the cardiac device 200 and controlling the operation of the devices using a monitor 341 and keyboard. The user interacts with a user interface module 304 to instruct the devices to transfer collected data from the cardiac device, to input additional patient data, to train the neural network and generate an updated set of neural network node coefficients, and to upload the updated set of values to the cardiac device 200.

Figure 4:
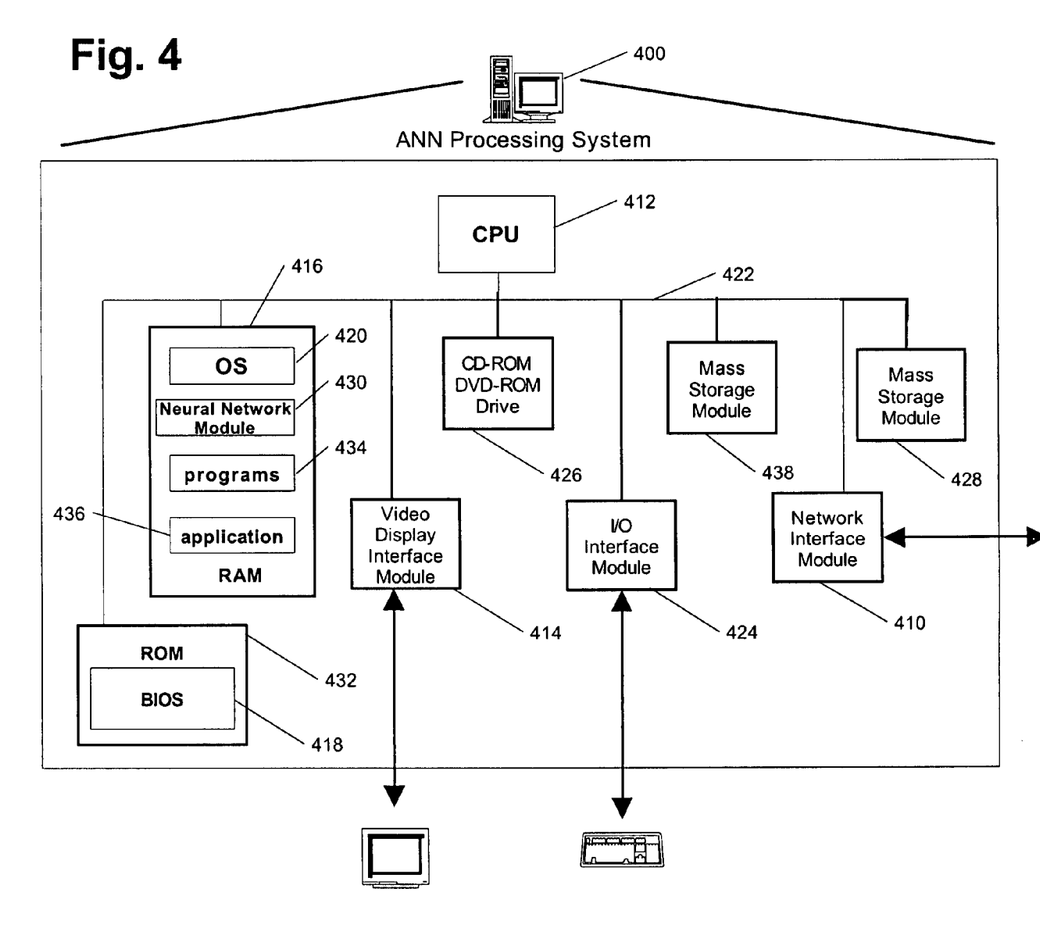
FIG. 4 illustrates a computing system that may be used to construct various computing systems that may be part of a distributed processing and communications system according to one embodiment of the present invention.

FIG. 4 illustrates a computing system that may be used to construct various computing systems that may be part of a distributed processing and communications system according to one embodiment of the present invention. In an exemplary embodiment of a ANN processing system 400, computing system 400 is operative to provide a neural network training and data collection system. Those of ordinary skill in the art will appreciate that the neural network training and data collection system 400 may include many more components than those shown with reference to a computing system 300 shown in FIG. 3. However, the components shown are sufficient to disclose an illustrative embodiment for practicing the present invention. As shown in FIG. 3, neural network training and data collection system 300 is connected to a cardiac device 200, or other devices as needed. Those of ordinary skill in the art will appreciate that a network interface unit 410 includes the necessary circuitry for connecting neural network training and data collection system 400 to a network of other computing systems, and is constructed for use with various communication protocols including the TCP/IP protocol. Typically, network interface unit 410 is a card contained within neural network training and data collection computing system.

ANN processing system 400 also includes processing unit 412, video display adapter 414, and a mass memory, all connected via bus 422. The mass memory generally includes RAM 416, ROM 432, and one or more permanent mass storage devices, such as hard disk drive 428, a tape drive 438, CD-ROM/DVD-ROM drive 426, and/or a floppy disk drive. The mass memory stores operating system 420 for controlling the operation of ANN processing system 400. It will be appreciated that this component may comprise a general purpose server operating system as is known to those of ordinary skill in the art, such as UNIX, MAC OS™, LINUX™, or Microsoft WINDOWS NT®. Basic input/output system ("BIOS") 418 is also provided for controlling the low-level operation of processing system 400.

The mass memory as described above illustrates another type of computer-readable media, namely computer storage media. Computer storage media may include volatile and nonvolatile, removable and non-removable media implemented in any method or technology for storage of information, such as computer readable instructions, data structures, program modules or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The mass memory also stores program code and data for providing a software development and neural network analysis and training system. More specifically, the mass memory stores applications including neural network based training program 430, programs 434, and similar analysis tool applications 436. ANN processing program 400 includes computer executable instructions which are executed to perform the logic described herein.

ANN processing system 400 also comprises input/output interface 424 for communicating with external devices, such as a mouse, keyboard, scanner, or other input devices not shown in FIG. 4. Likewise, ANN processing system 400 may further comprise additional mass storage facilities such as CD-ROM/DVD-ROM drive 426 and hard disk drive 428. Hard disk drive 428 is utilized by ANN processing system 400 to store, among other things, application programs, databases, and program data used by ANN processing system application program 430. The operation and implementation of these databases is well known to those skilled in the art.

Figure 5:
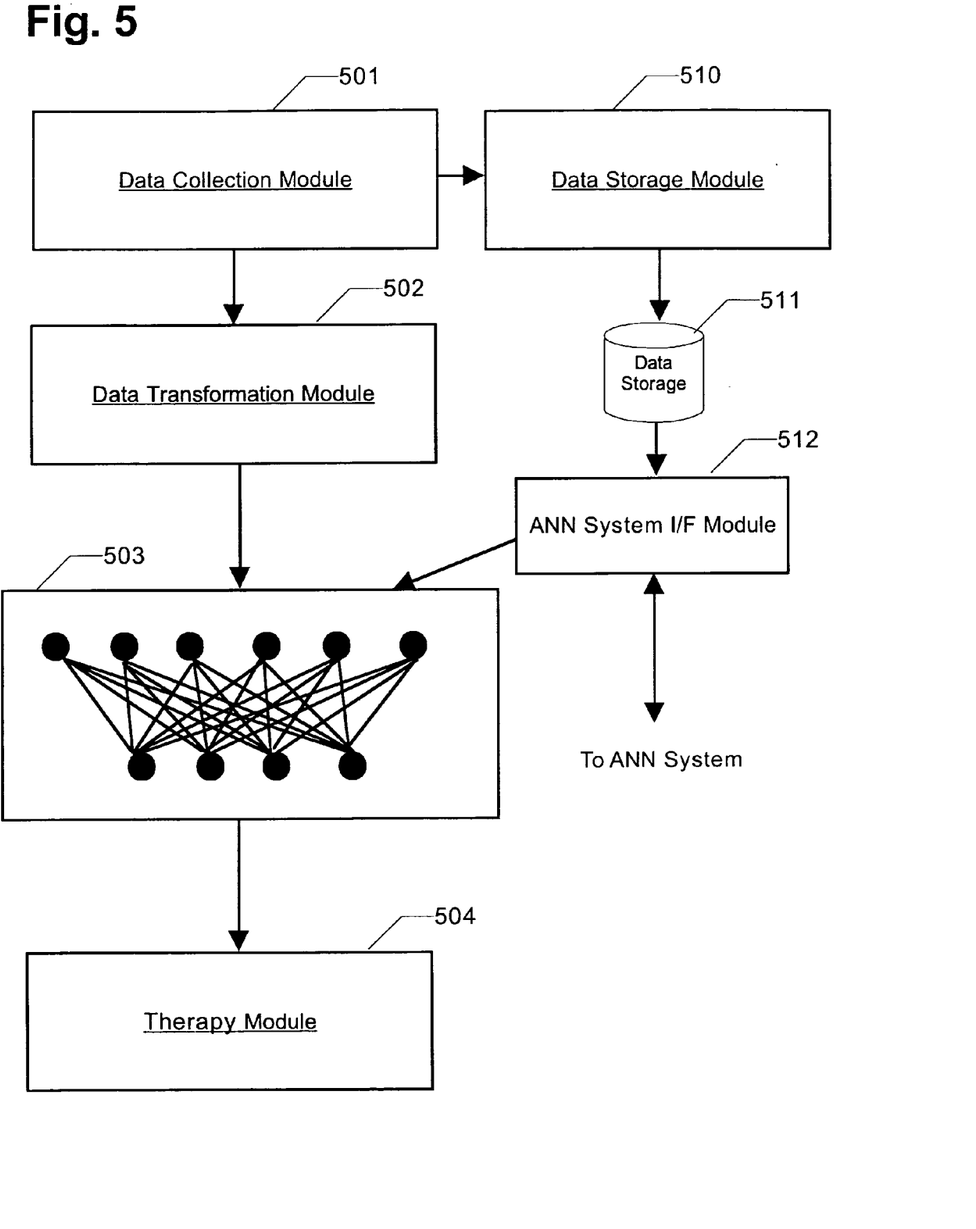
FIG. 5 illustrates another example embodiment of a cardiac device module showing data flow through a system for providing adaptive treatment therapies utilizing a neural network based learning engine according to one possible embodiment of the present invention.

FIG. 5 illustrates another example embodiment of a cardiac device module showing data flow through a system for providing adaptive treatment therapies utilizing a neural network based learning engine according to another example embodiment of the present invention. As discussed above with respect to FIG. 3, a cardiac data collection module 501 obtains data from electrical signals measured on a patient's heart 100. This data may include any number of observable parameters including values for an A Rate, a V Rate, an A Rate dispersion, a V Stability, an AV pattern, an NSR template, an arrhythmia template, a detected or classified depolarization morphology, a measure of patient activity such as derived from a Minute Ventilation (MV) sensor and/or an accelerometer, a measure of hemodynamic function such as derived from a hemodynamic sensor, a number of past attempts required to treat a given observed condition, an identification of a particular therapy that provided an effective treatment of an observed condition, an identification of a particular therapy that provided an ineffective treatment of an observed condition, an age of a patient, an identification of medications known to be taken by the patient, etc. This collected data may be passed to a cardiac data storage module 510 for storage into a local data store 511 for later use after being transmitted to the ANN processing system 300 by a ANN system interface module 512.

This data may also be passed to a cardiac data transformation module 502 that combines one or more of the above collected data values into a set of one or more health indications for use by the artificial neural network runtime module 503. For example, the collected data values may be combined to generate a health state of the patient's heart 100 that possesses various values such as good, average and bad, poor or similar state classifications. These classifications may then be used by the ANN runtime module 503 to generate an appropriate therapy, if any, is to be applied to the patent's heart.

Of course, one skilled in the art will recognize that the transformation module 502 may be eliminated in its entirety and the collected data used by the ANN runtime module 503 without deviating from the spirit and scope of the present invention as recited within the attached claims. The elimination of the transformation module 502 may increase the complexity of the neural network used within the cardiac device as well and the processing needed to utilize such a network. However, the use of the transformation module 502 reduces the amount of data available to the ANN runtime module, and as such may reduce the accuracy of the prediction function associated with selecting an optimal therapy.

The ANN runtime module 503 uses the data received from the transformation module 502 to generate commands to a therapy module 504 that provides the course of therapies provided to a patient. As discussed above, these may include pacing, ATP, low energy therapy and max energy therapy depending upon the observed data.

Figure 6:
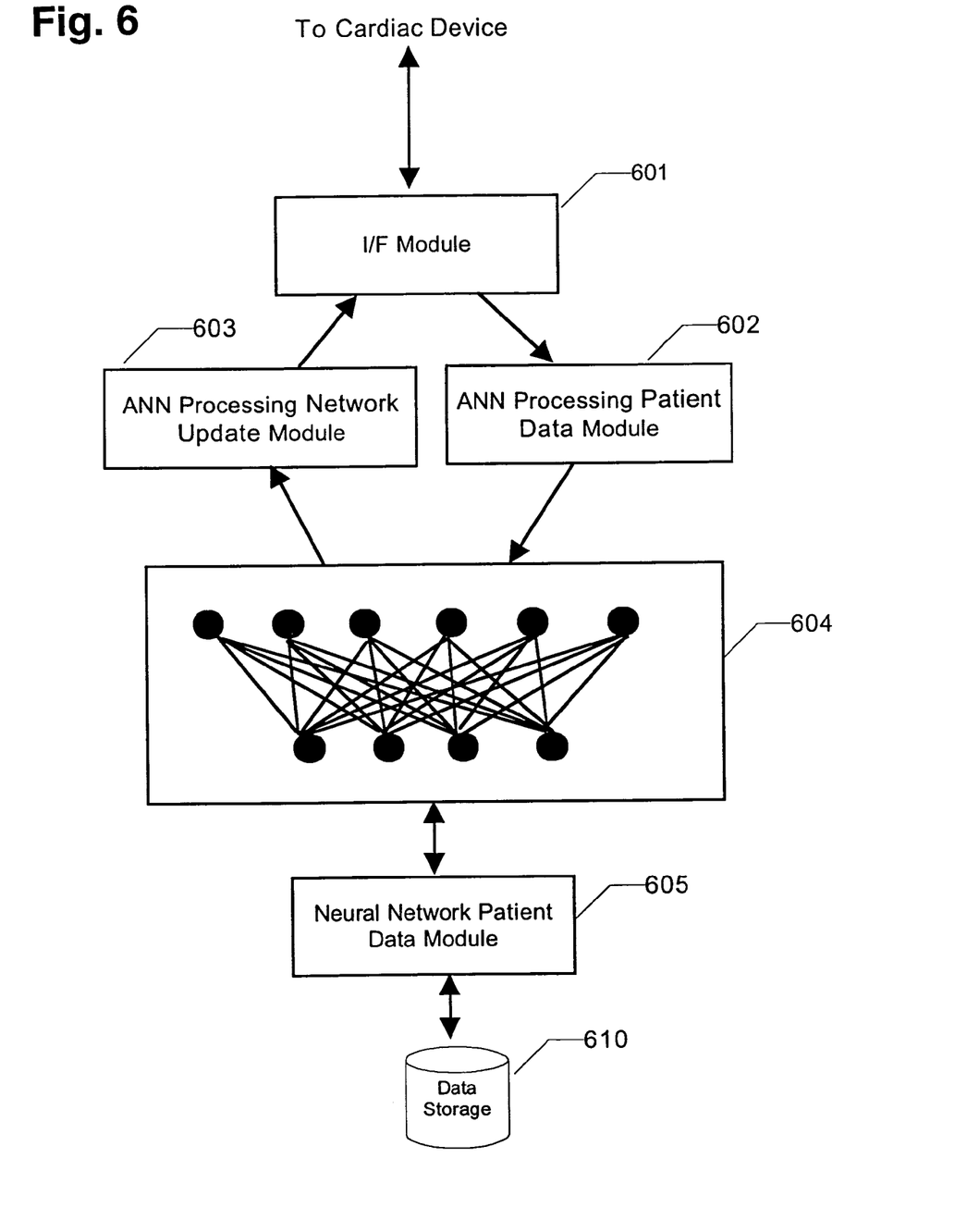
FIG. 6 illustrates another example embodiment of an artificial neural network server module for use with a cardiac device module showing data flow through a system for providing adaptive treatment therapies utilizing a neural network based learning engine according to one possible embodiment of the present invention.

FIG. 6 illustrates another example embodiment of an artificial neural network server module for use with a cardiac device module showing data flow through a system for providing adaptive treatment therapies utilizing a neural network based learning engine according to another possible embodiment of the present invention. The ANN processing system receives collected patient data from the cardiac device 200 through a cardiac device interface module 601 for use in training an artificial neural network resident both in the cardiac device as well as the ANN processing system 300. Typically, this operation occurs in a medical facility on a periodic basis as a patient seeks to optimize the operation of the cardiac device module 200. The frequency of these update operations may vary from patient to patient depending upon a number of factors including the nature of the cardiac problems of the particular patient, any changes in the nature of the cardiac problems of the particular patient, and the effectiveness of the adaptive treatment therapies provided by the cardiac device module for the particular patient.

The collected patient data is passed to an ANN patient data processing module 602 which performs preprocessing and data transformation similar to processing that occurs in the cardiac device module 200. Once the data has been preprocessed as needed, the data is passed to an artificial neural network module 604 to update and train the neural network. This neural network module 604 includes any training and validation modules needed to calculate the coefficients associated with the nodes within the neural network. The form and operation of the neural network module exactly matches the nodes in the runtime neural network located within the cardiac device module 200. The artificial neural network module processes the collected patient data along with other data received from a therapy data store 610 using a patient data module 605 that defined the course of therapy used within the cardiac device 200. The patient data module 605 may also receive data from an operator of the ANN processing system 300 for use in training the neural network in the neural network module 604.

The coefficients associated with the nodes of the neural network are passed to an ANN processing network update module 603. This module 603 formats and passes the data updates to the cardiac device module 200 for use in providing adaptive therapies to patients. The update module 603 also interacts with the cardiac device interface module 601 to perform the data communications with the cardiac device module 200 over the communications link 400.

The sequence of possible therapies to be applied by the cardiac device module 200 may include any number of possible treatment options that are applied using a sequence of criteria. The rules and control over when any of the possible treatment options are applied to a patient is embedded within the operation of the artificial neural network. The runtime module in the cardiac device implements these possible treatment options through the application of the artificial neural network to patient data collected by the cardiac device module 200. One skilled in the art will recognize that a number of possible variations on the treatment options as applied to a given patient may arise utilizing the artificial neural network as recited herein within the attached claims without deviating from the spirit and scope of the present invention.

FIG. 4 illustrates an example of a suitable operating environment in which the invention may be implemented. The operating environment is only one example of a suitable operating environment and is not intended to suggest any limitation as to the scope of use or functionality of the invention. Other well known computing systems, environments, and/or configurations that may be suitable for use with the invention include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like.

The invention may also be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Processing devices attached to a communications network typically includes at least some form of computer readable media. Computer readable media can be any available media that can be accessed by these devices. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by processing devices.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

Additionally, the embodiments described herein are implemented as logical operations performed by a programmable processing devices. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

While the above embodiments of the present invention describe a distributed processing for providing adaptive medical therapies utilizing a neural network based learning engine, one skilled in the art will recognize that the use of a particular computing architecture for a display computing system and a web server are merely example embodiments of the present invention. It is to be understood that other embodiments may be utilized and operational changes may be made without departing from the scope of the present invention as recited in the attached claims.

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. The present invention is presently embodied as a method, apparatus, and article of manufacture for providing an ANN processing system 400 for providing adaptive medical therapies utilizing a neural network based learning engine.

What is claimed is:

1. A system providing adaptive medical therapies utilizing a neural network based learning engine to a cardiac patient, the system comprising:
    a cardiac device module for providing adaptive medical therapies to the patient, the cardiac device module comprises:
        a cardiac device data collection module for collecting patient data associated with the cardiac health state of the patient's heart;
        a cardiac therapy module for applying corrective medical therapies to the patient's heart upon detection of undesired health conditions; and
        a runtime neural network module for processing collected patient data to determine the corrective medical therapies to be applied using the cardiac therapy module;
    an artificial neural network processing module for training and validating the operation of a neural network, the artificial neural network processing module comprising:
        a cardiac neural network training module for processing collected patient data to determine a set of operating coefficients used by the artificial neural network when determining optimal treatment therapies;
        a cardiac device interface module for receiving collected patient data from the cardiac device module and for transmitting the set of operating coefficients used by the artificial neural network when determining optimal treatment therapies; and
        collected patient data history data store for maintaining all of the patient collected data history and treatment therapies; and
    a communications link between the cardiac device module and the artificial neural network processing module;
    wherein the cardiac device runtime neural network module and the neural network training module implement identical networks of nodes.

2. The system according to claim 1 wherein the cardiac device module further comprises:
    a collected patient data storage module for maintaining a copy of relevant collected patient data collected by the cardiac device data collection module; and
    an artificial neural network processing module interface module for transmitting collected patient data from the cardiac device module and for transmitting the set of operating coefficients used by the artificial neural network when determining optimal treatment therapies.

3. The system according to claim 2, wherein the artificial neural network processing module interface module further receives the set of operating coefficients used by the artificial neural network when determining optimal treatment therapies from the artificial neural network processing module.

4. The system according to claim 3, wherein the collected patient data comprises one or more data values associated with the current state of the patient's heart.

5. The system according to claim 4, wherein the one or more data values associated with the current state of the patient's heart comprise data values associated with an A Rate, a V Rate, an A Rate dispersion, a V Stability, an AV pattern, an NSR template, an arrhythmia template, sensed morphology, a number of past attempts required to treat a given observed condition, an identity of a particular therapy that provided an effective treatment of an observed condition or an identity of a particular therapy that provided an ineffective treatment of an observed condition.

6. The system according to claim 1, wherein the artificial neural network processing module further comprises:
    a user interface module for providing a medical technician with an ability to interact with the artificial neural network processing module and to input data associated with optimal treatment therapies into the artificial neural network processing module.

7. The system according to claim 6, wherein the artificial neural network processing module utilizes the cardiac device interface module for transmitting the set of operating coefficients used by the artificial neural network when determining optimal treatment therapies to the cardiac device module.

8. The system according to claim 1, wherein the communications link between the cardiac device module and the artificial neural network processing module is used to transmit collected patient data and the set of operating coefficients used by the artificial neural network when determining optimal treatment therapies between the cardiac device module and the artificial neural network processing module.

9. The system according to claim 8, wherein the communications link utilizes an RF communications channel.

10. The system according to claim 8, wherein the communications link utilizes an optical communications channel.

11. A method, comprising:
    forming a cardiac device module for providing adaptive medical therapies to a cardiac patient, including:
        forming a cardiac device data collection module for collecting patient data associated with the cardiac health state of the patient's heart;

forming a cardiac therapy module for applying corrective medical therapies to the patient's heart upon detection of undesired health conditions; and forming a runtime neural network module for processing collected patient data to determine the corrective medical therapies to be applied using the cardiac therapy module;

forming an artificial neural network processing module for training and validating the operation of a neural network, including:

forming a cardiac neural network training module for processing collected patient data to determine a set of operating coefficients used by the artificial neural network when determining optimal treatment therapies;

forming a cardiac device interface module for receiving collected patient data from the cardiac device module and for transmitting the set of operating coefficients used by the artificial neural network when determining optimal treatment therapies; and forming a collected patient data history data store for maintaining all of the patient collected data history and treatment therapies; and forming a communications link between the cardiac device module and the artificial neural network processing module;

wherein the cardiac device runtime neural network module and the neural network training module are formed to implement identical networks of nodes.

12. The method of claim 11, wherein forming an artificial neural network processing module includes forming the processing module as part of a data processing system external to the patient.

13. The method of claim 11, wherein forming a cardiac device module includes forming an implantable medical device.

14. The method of claim 11, wherein forming a collected patient data history data store includes forming a database.

* * * * *

UNITED STATES PATENT AND TRADEMARK OFFICE
CERTIFICATE OF CORRECTION

| | | |
|---|---|---|
| PATENT NO. | : 7,200,435 B2 | Page 1 of 1 |
| APPLICATION NO. | : 10/668428 | |
| DATED | : April 3, 2007 | |
| INVENTOR(S) | : Ricci et al. | |

It is certified that error appears in the above-identified patent and that said Letters Patent is hereby corrected as shown below:

On the Title page, in field (56), under "Other Publications", in column 2, line 4, delete "Diving" and insert -- Divining --, therefor.

In column 12, line 32, in Claim 5, after "condition" insert -- , --.

Signed and Sealed this

Fifth Day of June, 2007

JON W. DUDAS
*Director of the United States Patent and Trademark Office*